US00PP12361P2

(12) United States Plant Patent
Trujillo

(10) Patent No.: US PP12,361 P2
(45) Date of Patent: Jan. 22, 2002

(54) TARO CULTIVAR NAMED 'PA'LEHUA'

(75) Inventor: Eduardo E. Trujillo, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/425,785

(22) Filed: Oct. 22, 1999

(51) Int. Cl.[7] ..... A01H 5/00
(52) U.S. Cl. ..... Plt./258
(58) Field of Search ..... Plt./258

(56) References Cited

U.S. PATENT DOCUMENTS

| | | | | |
|---|---|---|---|---|
| PP6,000 | P | 9/1987 | Christensen | Plt./130 |
| PP6,895 | P | 7/1989 | Meilland | Plt./137 |
| 4,925,696 | A | 5/1990 | Slimak | 426/637 |
| 5,034,327 | A | 7/1991 | Takayama et al. | 435/240.4 |
| PP8,526 | P | 12/1993 | Wilfret | Plt./373 |
| 5,464,646 | A | 11/1995 | Huang et al. | 426/615 |
| PP10,466 | P | 6/1998 | Wilfret | Plt./373 |

OTHER PUBLICATIONS de la Pena R. S. "The University of Hawaii Taro Germplasm Nursery and Breeding Program" Proceedings of the Workshop on Taro and Tanier Modeling University of Hawaii Research Extension Series 136 pages 7–9, Aug. 1992.*

Whitney L. D. et al "Taro Varieties in Hawaii" Hawaii Agricultural Experiment Station bulletin No. 84 pages 1–86, Dec. 1939.*

* cited by examiner

*Primary Examiner*—Bruce R. Campell
*Assistant Examiner*—Wendy C Baker
(74) *Attorney, Agent, or Firm*—Medlen & Carroll LLP

(57) ABSTRACT

The present invention relates to a new and distinct variety of *Colocasia esculenta* (popularly known as taro) named 'Pa'lehua.' 'Pa'lehua' differs distinctively from other taro plants by its unique combination of resistance to taro leaf blight caused by *Phytophthora colocasiae*, tolerance to root rot caused by Pythium spp., vigorous growth, large mother corm size, and purple corm of very good poi and eating qualities.

6 Drawing Sheets

The present invention relates to a new and distinct variety of *Colocasia esculenta* (popularly known as taro) named 'Pa'lehua.' 'Pa'lehua' plants were produced by cross-pollination of the commercial cultivars 'Ngeruuch' and 'Maui Lehua,' selection of progeny for a single plant which exhibited desirable agronomic and disease resistance properties, and asexual reproduction of the selected plant using tissue culture and propagation of hulis. 'Pa'lehua' differs distinctively from other taro plants by its unique combination or resistance to taro leaf blight (TLB) caused by *Phytophthora colocasiae*, tolerance to root rot caused by Pythium spp., vigorous growth, large mother corm size, and purple corm of very good poi and eating qualities.

REPRODUCTION

'Pa'lehua' is a product of the taro-breeding program of the University of Hawaii, Honolulu, Hi. The 'Pa'lehua' cultivar was derived from a single plant which was selected from a cross between the Hawaiian taro cultivar 'Maui Lehua' (unpatented) and the Palauan taro cultivar 'Ngeruuch' (unpatented; also referred to as P10). Ancestry of both parents is unknown, except that 'Maui Lehua' belongs to the Group Lehua of Hawaiian-Polynesian taros and is susceptible to taro leaf blight (TLB), caused by *Phytophthora colocasiae*, and 'Ngeruuch' is a Microneasian taro from Palau and is highly resistant to this disease.

'Maui Lehua,' the preferred poi taro of Hawaii, was selected as the female parent; 'Maui Lehua' exhibits the desirable agronomic characteristics of absence of runners, less than 6 suckers per plant, and superior poi quality purple corm. 'Ngeruuch' was selected as the pollen parent for its high resistance to the taro leaf blight disease; 'Ngeruuch' exhibits undesirable vegetative proliferation by long stolons.

Both parents are commercial cultivars. The initial cross-pollination of 'Ngeruuch' pollen and 'Maui Lehua' female flowers was made to produce a new poi taro having the agronomic characteristics of 'Maui Lehua' and the resistance to TLB of 'Ngeruuch.' $F_1$ progeny plants (including a single plant which was later designated 'Pa'lehua') were selected for their disease resistance to TLB, pocket rot, and basal rot, having fewer than 6 suckers and no runners, poi quality, and taste of cooked corms.

Asexual reproduction of 'Pa'lehua' was performed in Honolulu, Hi., by apical meristem multiplication using standard tissue culture procedures [Keolanui et al. (1993) Handbook for commercial-scale taro (*Colocasia esculenta*) tissue culture in Hawaii. University of Hawaii, College of Tropical Agriculture and Human Resources, Research Extension Series 145]. The traits of the plants which were generated by apical meristem multiplication were identical to those of the plant from which they were sexually reproduced. Cloned and rooted tissue culture plants of 'Pa'lehua' were produced at the University of Hawaii at Manoa, Honolulu, Hi.

Rooted tissue culture plants were grown to hulis to produce plants for field-testing as follows. Rooted tissue culture plants were transplanted from rooting medium to Sunshine Mix 4 potting soil. Potting mix (10 cubic inches volume) was used per plant in Compak® 606 multi-pots 3.25" deep with cell opening 2.25"×2" (T.O. Plastics Inc., 78th Street, Mpls, Minn. 55425). The Sunshine Mix 4 was mixed thoroughly with 2 lb of fast acting granular lime (The Chas H. Lilly Co, Portland, OR 97283) and 0.5 lb of Osmocote slow release fertilizer 14-14-14 (Scotts-Sierra Horticultural Products Co., 14111 Scottslawn Rd., Marysville, Ohio 43042) per cubic yard prior to use. The cells were placed in T.O. Plastics trays without holes 20.25"×15.75"×2.5" in size, containing a liquid nutrient solution made with one teaspoon of Peters (Scotts-Sierra) all-purpose soluble plant food 20-20-20/gallon of water. Plants were grown for 3–4 months in a greenhouse at 28° C. until the stem base of the plants was one inch in diameter and the plants were ready for field planting.

Plants were also progated in Hakalau, Hi., by the farming practice known as huli production whereby the apical shoots are separated from the rhizomes by cutting the shoot at the top of the corm immediately above the newest leaf scar and planted. A large number of plants of the new variety have been reproduced by this method and the resulting plants have exhibited the distinguishing characteristics of the original plant which was used for asexual propagation, indicating that the new 'Pa'lehua' cultivar is established.

CHARACTERISTICS

Figure 1:
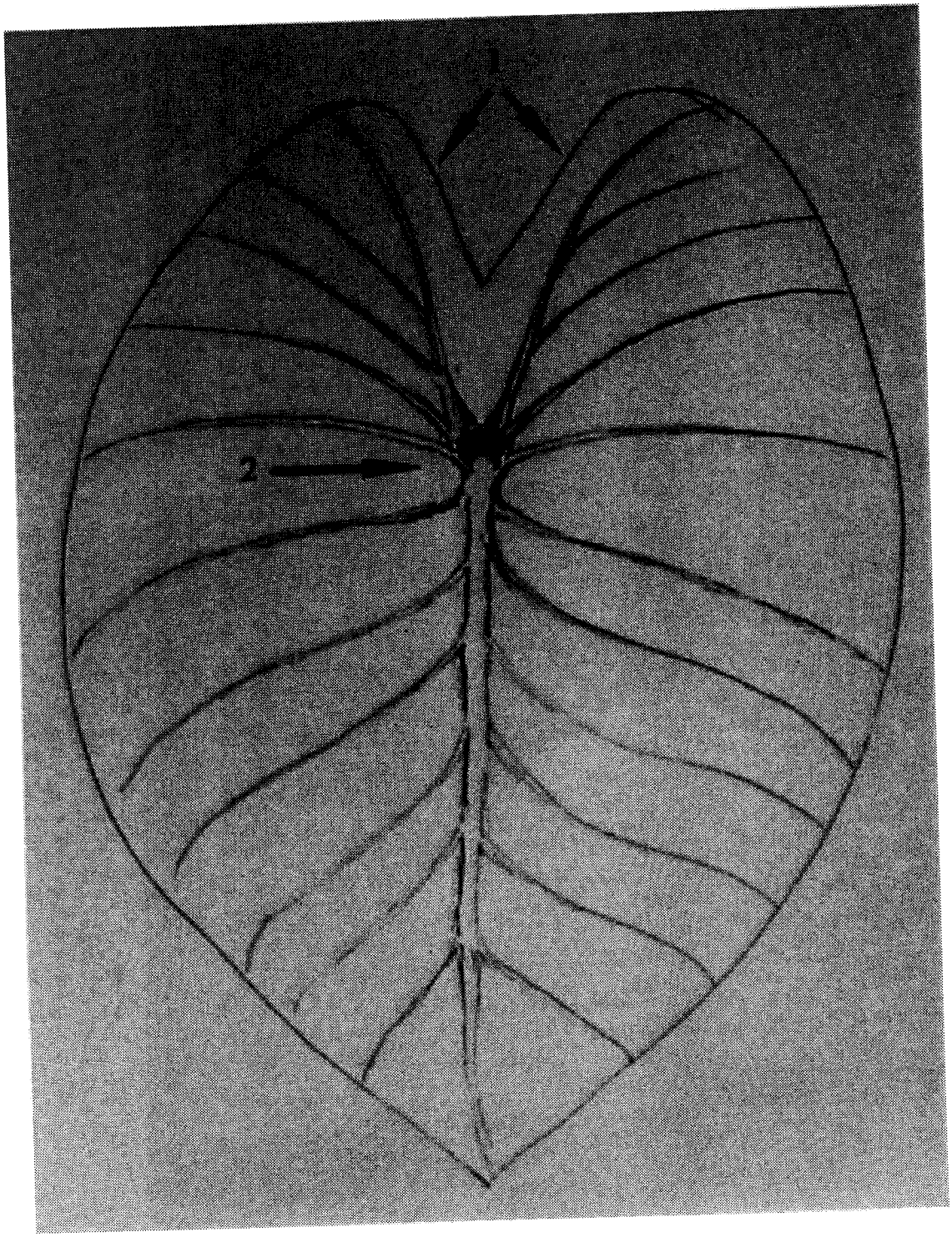
FIG. 1 is a diagram of a leaf which has been laid flat on a horizontal surface, showing the broadly ovate heart shaped outline, the piko (2) (point of attachment of petiole to the lamina) and the deep broadly acute to right angled sinus (1) between the lobes of the leaf on 'Pa'lehua.'

The asexually reproduced 'Pa'lehua' cultivar has several desirable horticultural characteristics, including resistance to taro leaf blight caused by *Phytophthora colocasiae*, tolerance to root rot caused by Pythium spp., vigorous growth, large mother corm size, and purple corm of very good poi and eating qualities. 'Pa'lehua' plants are suitable for both upland culture and wetland culture.

Resistance of 'Pa'lehua' to TLB was measured in field experiments at the Hakalau Farm and Nursery in Hamakua, Hi., which is located at a 600 ft elevation, receives high precipitation, and has a high incidence of TLB. Four subplots of 'Pa'lehua' were planted at 2 elevations in Hamakua, Hi. Each subplot contained 4 rows spaced 4 ft apart with 10 plants/row at a distance of 2 ft between plants. A randomized plot design was used for these tests. Disease assessment consisted of a visual determination of the percent area of foliar TLB damage caused by *Phytophthora colocasiae*. This data is shown in Table 1.

TABLE 1

Percent area of Foliar Damage Caused by *Phytophthora colocasiae*[1]

| Cultivar | First Experiment | Second Experiment | Third Experiment |
|---|---|---|---|
| 'Maui Lehua' | 0.2069 a | 0.2856 a | 0.2800 a |
| 'Pa'lehua' | 0.0418 bc | 0.0629 bcd | 0.0565 b |
| 'Ngeruuch' | 0.0153 c | 0.0320 d | 0.0194 b |

[1]Means with different letters are significantly different from one another, P ≦ 0.05 (Tukey's LSD test)

Table 1 shows that 'Pa'lehua' shows a significantly high degree of resistance to TLB which is similar to that exhibited by 'Ngeruuch' and which is much greater than that observed by 'Maui Lehua.' 'Pa'lehua' older leaves show symptoms of hypersensitive reaction when affected by taro leaf blight disease.

Corm yield was also measured in plants planted and harvested in Hamakua, Hi. The mean yield of the main corm of 'Pa'lehua' and 'Maui Lehua' was 3.8438 pounds/plant (i.e., 27,900 pounds/acre) and 2.4458 pounds/plant (i.e. 19,126 pounds/acre), respectively. The difference in corm yield was significant at P≦0.05 using Tukey's LSD test.

'Pa'lehua' was tolerant to root rot caused by Pythium spp. as distinguished from 'Maui Lehua' which is susceptible to root rot and from 'Ngeruuch' which is resistant to root rot. The number of suckers (3-2) produced by 'Pa'lehua' was significantly lower than the number (5-4) produced by 'Ngeruuch.'

Poi quality was measured by determining the stickiness, smoothness, viscosity, taro aroma intensity, and sweetness of the steamed or boiled corm which had been ground and mixed with water to 20% total solids. Desirable poi quality characteristics include a smooth texture, sweet taste, a consistency similar to soft mashed potato, stickiness similar to tapioca pudding, and strong taro aroma. Poi produced from 'Pa'lehua' was more intense purple than from 'Maui Lehua' with very good poi quality comparable to that of 'Maui Lehua.'

Eating quality was measured by determining the starchiness, and consistency of baked or boiled corms, with a starchy and moist consistency being desirable characteristics. Eating quality of 'Pa'lehua' corm was very good.

DETAILED BOTANICAL DESCRIPTION

The following combination of traits distinguishes 'Pa'lehua' as a new cultivar from other taro cultivars, including the parent plants from which it was derived. The photographs closely approximate the colors of the plants. However, to further facilitate the identification of color, reference is made to the British Color Council and The Royal Horticultural Society, Horticultural Color Chart, except where general color terms of ordinary dictionary significance are obvious. Wherein dimensions, sizes and other characteristics are given, it is to be understood that such characteristics are approximations of averages set forth as accurately as practicable. The descriptions herein are from 3 to 6 month old specimens grown in Hakalau, Hi., as indicated.

Plant:

*Size.*—Medium-tall, with medium spread, reaching up to a maximum of 1.45 m and 1.75 m high at 3 and 6 months after planting, respectively. Mother plant pseudo-stem circumference at soil line is up to 35 to 42 cm at 3 and 6 months after planting, respectively. A mother plant is the plant material which is first introduced into the soil to begin taro production and which gives rise to a corm, herein referred to as "mother corm." Typically, this plant material contains part of the huli and 2–3 leaf blades. The corm of the mother plant produces rhizomes which give rise to daughter plants which begin to appear above soil level at about 4–5 months after planting of the mother plant. Plants were grown on silicate clay soils, with average daily temperature of 27° C., average rainfall of 150 inches/year and average solar radiation of 450 langley (Cal.sq. cm/day).

*Maturity.*—10–12 months from planting to harvest marketable corms.

*Quality.*—Poi quality 4–4.5 (scale of 1 to 5; 1=poor and 5=excellent). Eating quality 4.5 (scale same as above).

Leaves:

*Number.*—Usually a 3–7 month old mother plant maintains 5–6 leaves at a time, each new leaf being produced approximately every 10 days until the corm is ready to harvest.

*Size.*—Up to 81 cm and 93 cm long, and up to 55 cm and 60 cm wide on a 3- to 6-month old plants, respectively.

Figure 2:
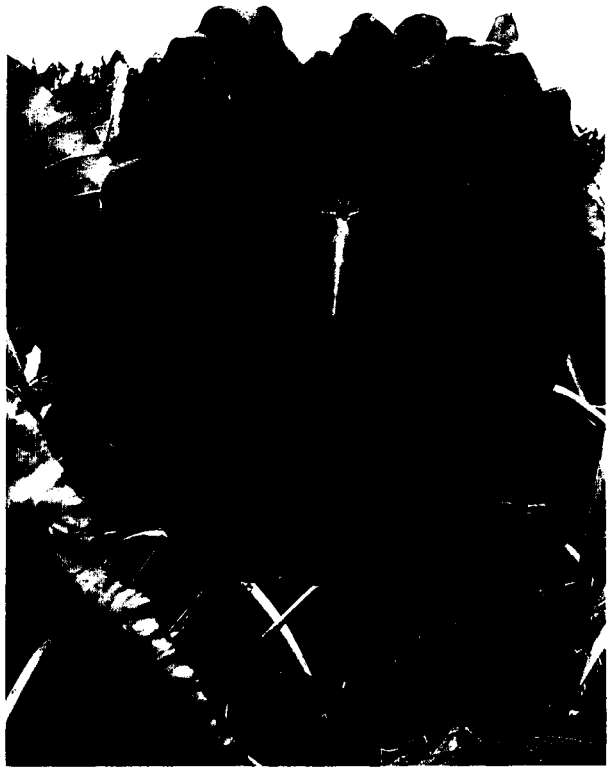
FIG. 2 is a photograph of the leaf abaxial surface of a 6-month old 'Pa'lehua' plant showing dark green lamina with an iridescent purplish tinge nd reddish-purple piko. Leaves measure up to 60 cm wide by 80 cm long and petioles up to 130 cm long.
Figure 6:
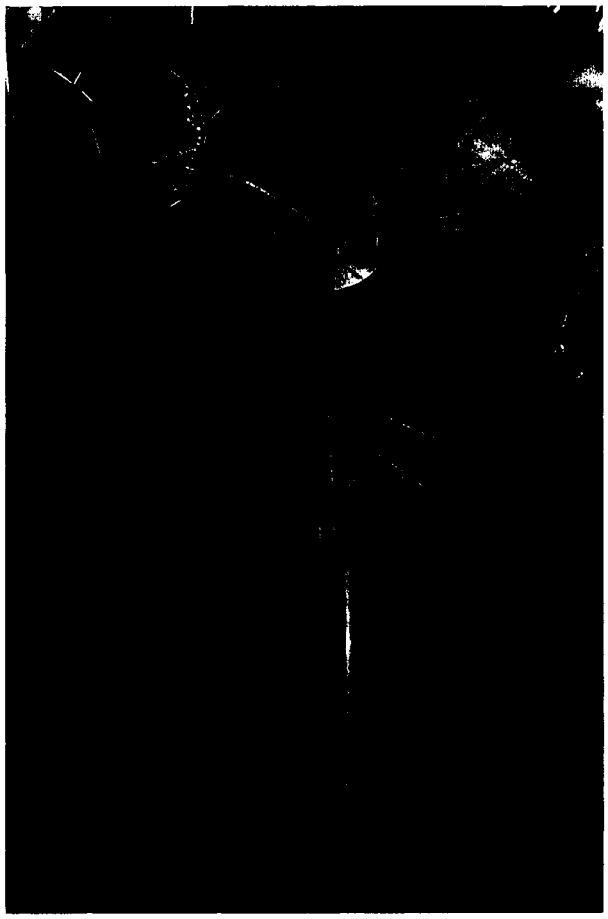
FIG. 6 is a photograph of the adaxial surface of 'Pa'lehua' leaf from a 7-month old plant showing light-green lamina with purple veins, and light-green pinkish petiole with bright purple upper portion.

*Shape.*—Sagittate-broadly-ovate blade with an acutely pointed apex, peltate leaf base and a deep, broadly acute to right angled sinus between lobes, up to 80° to 90°, peltated, erect, with apex down, and palmate-venation, with entire margins (FIGS. 1, 2, and 6). Lamina appendages are absent. Leaf surface is flat and open.

Figure 3:
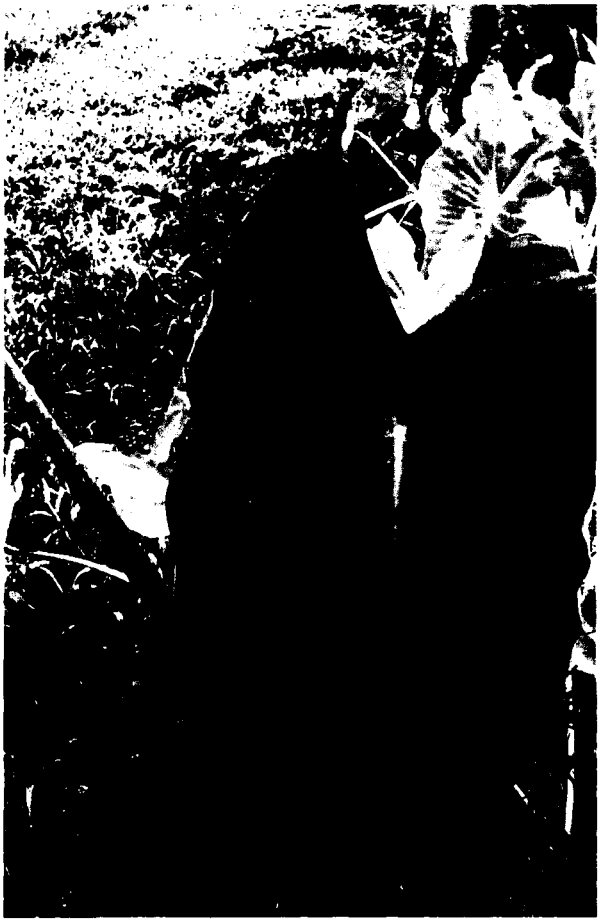
FIG. 3 is a photograph of a newly opened 'Pa'lehua' leaf blade showing light green coloration with a peach cast, salmon-pinkish veins, and portions of petioles which are light greenish pink with purple margins.
Figure 4:
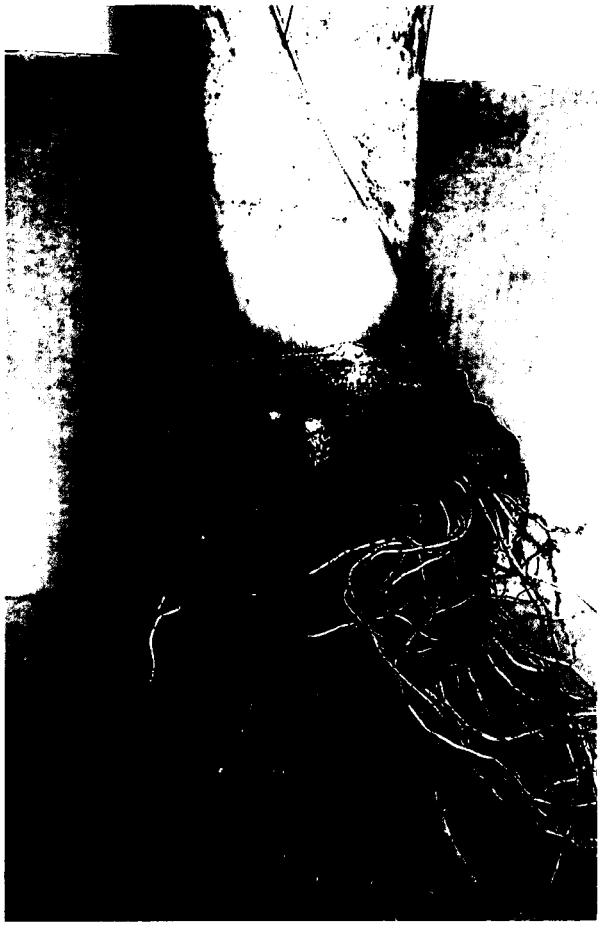
FIG. 4 is a photograph of 'Pa'lehua' mother plant showing lilac-purplish base of the huli, corm with purple skin, and roots.
Figure 5:
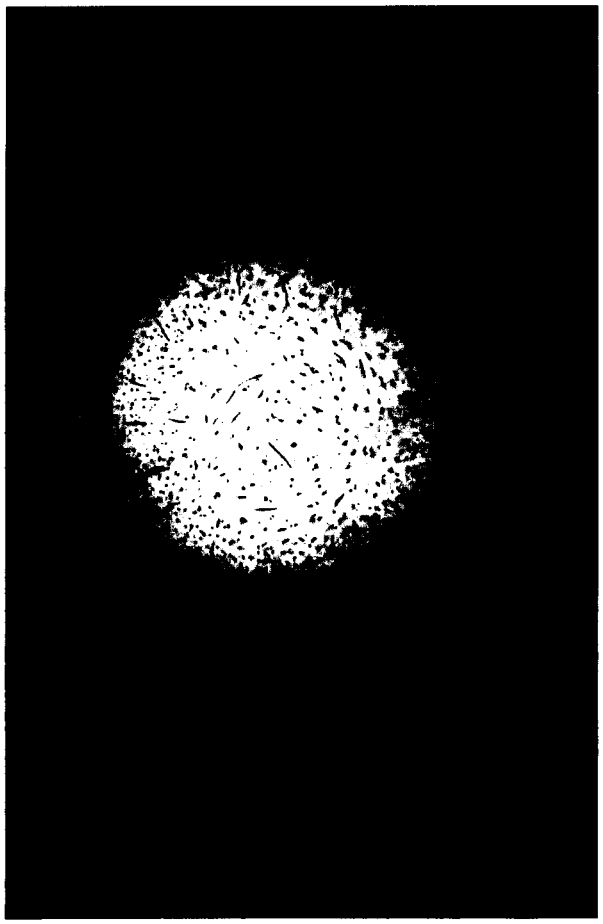
FIG. 5 is a photograph of a cross section of 'Pa'lehua' corm showing a lilac-purplish flesh with purple vascular strands.

*Color.*—Abaxial leaf surface is dark green (R.H.S. #135 A) with a tinge of iridescent purple. Point of attachment of petiole to lamina (piko) on abaxial surface of younger leaves is bright purple (R.H.S. #59 A) and on oldest leaf is violet (R.H.S. #83 A). The red piko dot resembles a Chinese pagoda in shape. All main veins on the abaxial surface are light salmon (R.H.S. #27 C). The adaxial leaf surface is light green (R.H.S. #138 B) and the veins are red-purple (R.H.S. #59 B) (FIG. 6). Young petioles are pinkish (R.H.S. #70 B) at base, up to 121 cm to 143 cm long, colored pea green (R.H.S. #145 C) with sheath margins being red-purple (R.H.S. #71 A). Sap of petiole cross section is red-purple (R.H.S. #60 B). Petiole attachment to adaxial surface of lamina is dark purple (R.H.S. 187 B). Young leaves are light green (R.H.S. #147 B) with a peach cast and salmon-pinkish (R.H.S. #27 A) veins (FIG. 3).

*Veins.*—Three large veins radiating from the piko, the largest vein is the midrib extending from the piko to the tip of the lamina with up to 8 pairs of secondary veins radiating from it. The other 2 shorter primary veins extend from the piko to the tip of the leaf lobes with 3 secondary veins radiating from each (FIG. 1). All main veins are light salmon (R.H.S. #27 C) on the abaxial surface of the leaf, and are dark purple (R.H.S. #187 A) on the adaxial surface.

Corms:

*Size.*—Main corm is large measuring 17 cm to 25 cm long with a diameter up to 14 cm to 17 cm at the widest cross-section and with thick roots.

*Shape.*—Ovate and free of pocket rot.

*Color.*—Outer skin tissue is garnet brown (R.H.S. #200 A), and upper leaf scars are orange-brown (R.H.S. #166 A). Flesh of corm on cross-section is lilac-purple (R.H.S. #76 C) with the outer 1 mm. being intense purple (R.H.S. #72 A) and with intense purple (R.H.S. #72 A) fibers. The corm flesh color is more intense than that of 'Maui Lehua' corm flesh. Roots are purplish (R.H.S. #59 D).

*Weight.*—Corm weight of mother plant is from 1.8 to 2.8 kg.

Rhizomes: The mother corm produces 3–4 suckers on closely attached rhizomes approximately 4–5 months after planting the huli. The daughter plant corms at harvest weigh 0.2–0.5 kg. the outer skin tissue of the daughter corm is garnet-brown (R.H.S. #200 A) and upper leaf scars are orange-brown (R.H.S. #166 A). Flesh of corm on cross-section is lilac-purple (R.H.S. #76 C) with the outer 1 mm being intense purple (R.H.S. #72 A).

Inflorescence: Normally not produced.

I claim:

1. A new and distinct variety of taro plant, substantially as illustrated and described herein, that is characterized by resistance to taro leaf blight caused by *Phytophthora colocasiae*, tolerance to root rot caused by Pythium spp., vigorous growth, large mother corm size, and purple corm of very good poi and eating qualities.

* * * * *

Disclaimer

PP. 12,361 P2—Edwardo E. Trujillo, Honolulu, HI (US). TARO CULTIVAR NAMED 'PA'LEHUA'. Patent dated Jan. 22, 2002, Disclaimer filed June 16, 2006, by the Assignee, University of Hawaii.

This patent is subject to a terminal disclaimer.

*(Official Gazette, September 12, 2006)*